United States Patent [19]

Segawa

[11] Patent Number: 4,539,995
[45] Date of Patent: Sep. 10, 1985

[54] X-RAY TRANSMISSIVE ELECTRODE-SHIELDED WIRE ASSEMBLY

[75] Inventor: Kiyoshi Segawa, Tokyo, Japan

[73] Assignee: Fukuda Denshi Kabushiki Kaisha, Tokyo, Japan

[21] Appl. No.: 567,397

[22] Filed: Dec. 30, 1983

Related U.S. Application Data

[62] Division of Ser. No. 291,031, Aug. 7, 1981, Pat. No. 4,442,315.

[30] Foreign Application Priority Data

Nov. 17, 1980 [JP] Japan ................................ 55-160689
Nov. 17, 1980 [JP] Japan ................................ 55-160690

[51] Int. Cl.$^3$ ................................................ A61B 5/04
[52] U.S. Cl. ........................................ 128/639; 174/36
[58] Field of Search .............................. 128/639–641, 128/643, 644; 174/36

[56] References Cited

U.S. PATENT DOCUMENTS

| | | | |
|---|---|---|---|
| 4,122,843 | 10/1978 | Zdrojkowski | 128/644 |
| 4,155,354 | 5/1979 | Rasmussen | 128/640 |
| 4,353,372 | 10/1982 | Ayer | 128/640 |
| 4,370,984 | 2/1983 | Cartmell | 128/640 |

Primary Examiner—Lee S. Cohen
Attorney, Agent, or Firm—Edward F. Levy

[57] ABSTRACT

An electrode and a lead wire therefor used with a device for measuring the electrical signals emanating from a living body, such as a cardiograph or electroencephalograph employed for examination and diagnostic purposes. The electrode consists of two layers of finely divided electrically conductive material, that are printed in laminated fashion on the opposite surfaces of an insulating film. The lead wire comprises plural laminated layers of finely divided electrically conductive material on the opposite sides of an insulating film, the laminated layers being interspersed with or encased by carbon layers and insulating layers. Since X-rays penetrate the electrode and the lead wire, an X-ray photograph may be taken during visual inspection of the biosignals without the image of the electrode and the lead wire appearing on the film to hinder diagnosis.

5 Claims, 11 Drawing Figures

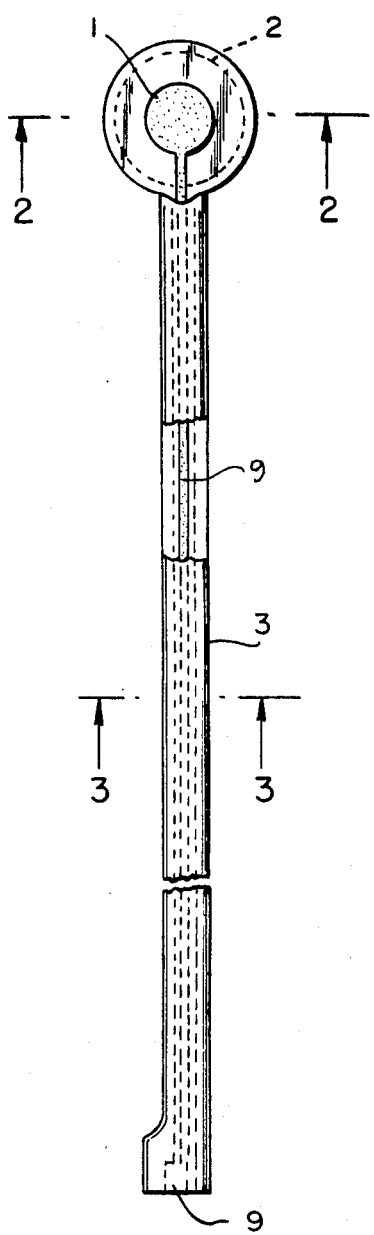
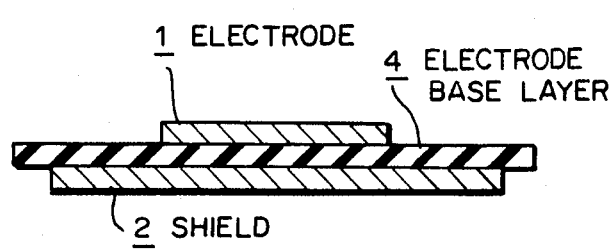
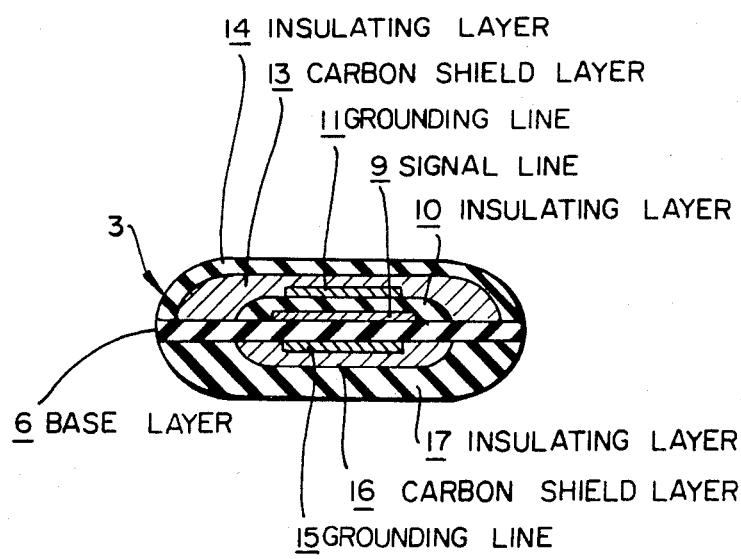

X-RAY TRANSMISSIVE ELECTRODE-SHIELDED WIRE ASSEMBLY

This is a division of application Ser. No. 291,031, filed Aug. 7, 1981, issued Apr. 10, 1984, as U.S. Pat. No. 4,442,315.

BACKGROUND OF THE INVENTION

1. Field of the Invention

This invention relates to an electrode and a lead wire therefor used for taking a cardiogram or an electroencephalogram, and more particularly to an X-ray transmissive electrode and a lead wire therefor suitably used for taking an X-ray photograph while the electrode remains attached to the body of a patient, and to a method of manufacturing the same.

2. Description of the Prior Art

Heretofore, metallic electrodes and shielded wire were used for the extraction of biosignals for preparation of a cardiogram or the like. The metallic electrode was brought into contact with the patient's body as by use of an adhesive, and one end of the electrode was connected to the electrically conductive core of the shielded wire, with the shield portion provided around the metallic electrode being connected to the shielded portion of the shielded wire to prevent electrostatic or electromagnetic noise from mixing with the biosignals.

Furthermore, when taking an X-ray photograph during measurement, the electrode had to be removed from the patient's body to prevent the image of the electrode from appearing on the photographic film. Such adverse effects may be reduced by having the size of the electrode and the diameter of the shielded wire extending from the electrode as small as possible. However, certain areas desired to be photographed were still masked by the electrode and the shielded wire, thus interfering with accurate X-ray photography and proving a hindrance to diagnosis.

It may be desired from time to time to take an X-ray photograph while visually inspecting the waveshape of the cardiogram or electroencephalogram. In this case, since the electrode and the shielded wire cannot be removed from the patient's body, indistinct portions may appear on the photograph due to obstructions presented by the electrode and the shielded wire. In order to overcome such problems, electrodes penetrable by X-rays have been devised. For instance, the Japanese Patent Application Laid-Open No. 118873/1977 discloses such an X-ray transmissive electrode comprizing an extremely thin gold layer deposited on a Mylar (polyethylene telephthalate) plastic base film. The electrode is connected to a single core copper wire clamped and reinforced by a plastic tape. Japanese Patent Application Laid-Open No. 118989/1977 and 93681/1978 both disclose substantially carbon electrodes for biological use. It is contemplated that X-ray transmissive electrodes for biological use may be obtained by using carbon fibers or very thin carbon layers. However, there has not yet been devised an X-ray transmissive electrode and a shielded wire that may be produced easily and at minimal cost.

SUMMARY OF THE INVENTION

It is therefore an object of the present invention to provide an electrode and shielded wire of a sturdy construction wherein the shielded wire and the electrode may be integrally made as one unit or assembly from the same materials.

Another object of the present invention is to provide an electrode and a shielded wire therefor that are very thin, resilient and compact in size.

A further object of the present invention is to provide an X-ray transmissive electrode and shielded wire therefor which may be produced by a printing technique and which thus lend themselves the mass production.

A still further object of the present invention is to provide a shielded wire that may be connected easily to the connectors of measuring equipment, one surface of the wire being used as a signal line and the other surface thereof as a grounding line.

This invention comprises an electrode and a shielded wire both formed integrally on an insulating sheet or film. The sheet or film is disc-shaped at the portion which contacts the patient's body, and strip-shaped at the shielded wire portion. On one surface of the disc-like portion of the insulating sheet, there is provided an electrode consisting essentially of a layer of finely divided electrically conductive material. On the other surface of the disc-like portion is a shielded layer having a larger area than that of said electrode.

On one surface of the strip portion of the insulating sheet which is continuous to and integral with the disc-like portion, there is a band-like layer of finely divided electrically conducting material, which is also continuous and integral with the layer of the finely divided electrode material. The band-like layer of the finely divided conductive material is used as a signal line. Above this signal line is formed an insulating layer. Overlying the insulating layer and the signal line is a grounding line made of finely divided electrically conductive material, the grounding line being in turn encircled by a carbon layer to complete the shielding. The electrically conductive material and the insulating layer are provided on the strip portion of the insulating sheet by printing to facilitate the manufacturing process.

BRIEF DESCRIPTION OF THE DRAWINGS

These and other objects, features and advantages of the invention will be more fully apparent from the following detailed description of a preferred embodiment of the invention taken in conjunction with the accompanying drawings wherein like reference characters refer to like parts throughout and in which:

FIG. 1 is a plan view of the electrode and shielded wire assembly or unit of the present invention;

FIG. 2 is a cross-sectional view solely of the electrode of the present invention;

FIG. 3 is a cross-sectional view solely of the shielded wire of the present invention.

DESCRIPTION OF THE PREFERRED EMBODIMENT

Figure 4A:
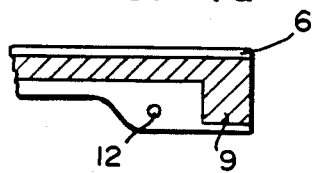
FIGS. 4a to 4e are top plan views, partially broken away, of one end portion of a base layer of shielded wire showing the successive printing of layers of conductive lines and insulating material thereon to form the shielded lead wire 3 of FIG. 1.

Referring to FIG. 1, an electrode of the present invention comprises a flat electrode portion 1 in the form e.g. of a disc and a flat shield portion 2 covering this electrode portion 1. A shielded lead wire 3 is extended from the electrode portion 1 and the shield portion 2.

Referring to FIG. 2, the electrode portion 1 consisting essentially of fine particles of electrically conductive material and readily penetrable by X-rays is applied, as by coating or printing, on to one surface of a base layer 4 consisting of an insulating film e.g. of synthetic material also penetrable by X-rays. The shield portion 2 is applied by depositing, coating or printing carbon on the opposite surface of the base layer 4.

The construction of the inventive shielded wire and the method for manufacture of the same will be explained by referring to FIGS. 3 and 4a through 4h. In FIGS. 4a through 4e, one end portion of a base layer 6 for a shielded wire opposite the end connected to the electrode 1 is shown in top plan view, while in FIGS. 4f through 4h, the same end portion is shown in bottom plan view, that is, as seen from the direction opposite to that of FIGS. 4a through 4e. The progressive application of layers of conductive material and insulation is shown successively in these views.

Figure 4B:
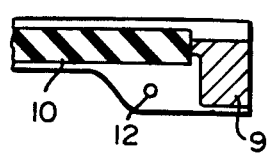
Figure 4C:
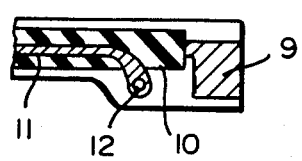
Figure 4D:
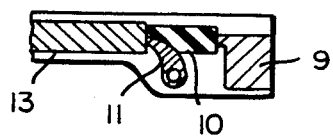
Figure 4E:
Figure 4F:
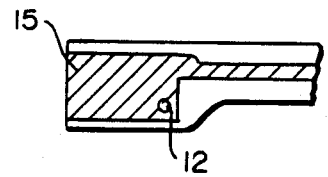
FIGS. 4f to 4h are bottom plan views of the base layer of FIGS. 4a–4e, showing the successive printing of layers of conductive lines and insulating material thereon.
Figure 4G:
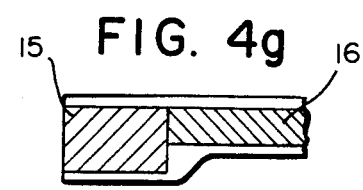
Figure 4H:

A signal line 9 is first applied to a base layer 6 integrally connected to the base layer 4. An electrically conductive paste is used as the material for signal line 9, the line 9 being printed on the base layer (see FIG. 4a). Then, a layer of an insulating material 10 is printed over the signal line 9 (FIG. 4b). A further layer of electrically conductive paste is printed over the insulating material 10 for providing a grounding line 11 (FIG. 4c). Some of the paste of the grounding line 11 intrudes into small holes 12 in the base layer 6, one of such holes being shown in FIGS. 4a through 4c. The conducting material of the grounding line 11 is thus conveyed through these holes 12 to the reverse surface of the base 6 for providing so-called through-holes. A carbon layer 13 is printed on the grounding line 11 for shielding (FIG. 4d). An insulating layer 14 is further printed on the carbon layer 13 (FIG. 4e). On the reverse face of the base 6, an electrically conductive paste is printed as a grounding line 15 (FIG. 4f). Since the conductive paste is applied in this way to the opposite ends of the small holes 12, the grounding lines 11, 15 are connected together via the holes 12. A carbon layer 6 is printed over the grounding line 15 (FIG. 4g) and an insulating layer 17 is further printed on the carbon layer 16 (FIG. 4h) to complete the shielded wire. As apparent from FIG. 4, since the signal line 9 is provided on one surface of the base layer 6 and the grounding line 15 is provided on the other face of the base layer 6, the shielded wire may be connected to the input terminals of measuring equipment with the aid of suitable connectors.

The shielding operation of the inventive shielded wire will be explained with reference to FIG. 3.

The shielding of the signal line 9 is effected by the two grounding lines 11, 15 and carbon layers 13, 16 positioned to encircle the signal line 9. Thus, on the outside of the grounding lines 11, 15, there are provided the carbon layers 13, 16 over a width to completely overlie the signal line 9, these carbon layers 13, 16 being in electrical contact with the grounding line 11, 15 to prevent the intrusion of external noise into the signal line 9.

The operation of the inventive X-ray transmissive electrode will now be explained with reference to FIGS. 1 through 3.

The electrode portion 1 is placed in contact with a portion of the patient's body. An electrically conductive adhesive material may optionally be coated onto the surface of the electrode portion 1 for maintaining optimum contact between the portion 1 and the patient's body. The signal current from the patient's body, obtained through the electrode portion, is transmitted by the signal line 9 of the lead wire 3. The shield carbon portion 2 is connected to the grounding lines 11, 15 of the lead wire 3. Since the signal line 9 is surrounded via insulating layer 10 by the grounding lines 11, 15 and the electrically conductive carbon layers 13, 16 surrounding these grounding lines 11, 15, the signal current emanating from the patient's body is transmitted along the signal line 9 without mixing with external electrostatic or electromagnetic noise. The grounding lines 11, 15 may be connected electrically with the carbon layers 13, 16 with the aid of small holes 12 at the end or at intermediate portions of the lead wire 3 as shown in FIGS. 4a, 4b and 4f.

It is to be noted that any external noise may be passed to ground through the grounding lines 11, 15 and thus without interfering with signal transmission through the signal line. The electrode portion 1 is connected integrally to the signal line 9, the base layer 4 of the electrode is connected integrally with the base layer 6 of the lead wire 3 and the shield portion 2 is connected integrally to the earthing conductors 11, 15 of the lead wire 3. The carbon as well as synthetic materials and electrically conducting materials that constitute the electrode-shielded wire assembly of the present invention are penetrable by X-rays so that photography can be performed during visual inspection without the necessity of dismounting the electrode portion.

As described above, according to the present invention, the signal line 9 and the electrode portion 1 are formed continuously on one surface of the insulating base layers 4, 6. The signal line 9 is shielded by the carbon layers 13, 16 having larger widths than the width of the signal line 9. The grounding lines 11, 15 are located on opposite sides of the base layer 6 in such positions that that the carbon layers 13, 16 may contact the grounding lines 11, 15. The X-ray transmissive electrode-shielded wire assembly has excellent resiliency and an excellent shielding effect and may be mass produced at reduced cost.

What is claimed is:

1. An X-ray transmissive electrode-shielded wire assembly designed for extraction and transmission of electrical signals emanating from living bodies, said assembly comprising a base of an insulating sheet material comprising an enlarged portion and an integral elongated strip portion, an electrode and a narrow signal line both mounted on said base and made of electrically conductive material capable of being penetrated by X-rays, said electrode being formed on the surface of one side of said base at said enlarged portion, and said signal line being formed on the surface of the same side of said base strip portion and being electrically connected to said electrode, with said narrow signal line extending longitudinally along said base strip portion, a shielding layer of fine particles of electrically conductive material underlying said electrode and having an area larger than the area of said electrode, said shielding layer being adapted to shield said electrode and being mounted on the surface of the enlarged portion of said base opposite to the surface on which said electrode is mounted, a first layer of electrically conductive material having a width larger than the width of said signal line and arranged on said one side of said base strip portion overlying said signal line, a layer of insulating material located between said signal line and said first layer of electrically conductive material, a second layer of electrically conductive material having a width larger than the width of said signal line and arranged on the opposite side of said base strip portion underlying said signal line, and a first grounding line overlying said insulating layer and a second grounding line underlying said base strip portion, said first and second grounding lines being electrically connected to and arranged longitudinally of said first and second layers of electrically conductive material, said electrode shielding layer being electrically connected to said first and second grounding lines, said signal line being substantially shielded by said first and second layers of electrically conductive material and said first and second grounding lines.

2. An X-ray transmissive electrode-shielded wire assembly according to claim 1 in which said electrode and signal line are integrally formed of a continuous layer of electrically conductive material printed on the surface of said one side of said base.

3. An X-ray transmissive electrode-shielded wire assembly according to claim 2 in which said first and second layers of electrically conductive material comprise layers of fine particles of carbon.

4. An X-ray transmissive electrode-shielded wire assembly according to claim 3 in which said first grounding line comprises a layer of electrically conductive paste printed on the surface of said insulating layer remote from said signal line and in electrical contact with said first layer of electrically conductive material, and the second grounding line comprises a layer of electrically conductive paste printed on the surface of said opposite side of said strip portion in electrical contact with said second layer of electrically conductive material, said electrode shielding layer comprising a layer of electrically conductive material formed integrally with said second grounding line.

5. An X-ray transmissive electrode-shielded wire assembly according to claim 4 in which said signal line, grounding lines, and layers of electrically conductive material are made of materials capable of being penetrated by X-rays.

* * * * *